United States Patent
Pearl, Jr. et al.

(10) Patent No.: US 10,131,583 B2
(45) Date of Patent: Nov. 20, 2018

(54) SYSTEMS AND METHODS FOR ANALYZING THE CHARACTERISTICS AND COMPOSITIONS OF A DRY CEMENT

(71) Applicant: Halliburton Energy Services, Inc., Houston, TX (US)

(72) Inventors: William C. Pearl, Jr., Houston, TX (US); Megan Renee Pearl, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 63 days.

(21) Appl. No.: 15/313,246

(22) PCT Filed: Aug. 26, 2014

(86) PCT No.: PCT/US2014/052621
§ 371 (c)(1),
(2) Date: Nov. 22, 2016

(87) PCT Pub. No.: WO2016/032435
PCT Pub. Date: Mar. 3, 2016

(65) Prior Publication Data
US 2017/0183269 A1    Jun. 29, 2017

(51) Int. Cl.
*E21B 47/00*       (2012.01)
*C04B 28/02*       (2006.01)
(Continued)

(52) U.S. Cl.
CPC .......... *C04B 40/0096* (2013.01); *C04B 28/02* (2013.01); *C04B 28/04* (2013.01);
(Continued)

(58) Field of Classification Search
CPC ..... C04B 28/02; C04B 40/0096; C04B 28/04; C04B 28/14; C04B 28/34; C09K 8/42;
(Continued)

(56) References Cited

U.S. PATENT DOCUMENTS 7,697,141 B2    4/2010    Jones et al.
8,212,213 B2    7/2012    Myrick et al.
(Continued)

FOREIGN PATENT DOCUMENTS

| EP | 1057118 A1 | 12/2000 |
| GB | 1169387 A | 11/1969 |
| WO | 2016032435 A1 | 3/2016 |

OTHER PUBLICATIONS

Pearl, Megan, Rapid Classification of Imaged Objects Using Molecular Factor and Multivariate Optical Computing, Submitted in Partial Fulfillment of the Requirements for the Degree of Doctor of Philosophy in Chemistry & Biochemistry, 2011.
(Continued)

*Primary Examiner* — Zakiya W Bates
(74) *Attorney, Agent, or Firm* — Gilliam IP PLLC

(57) ABSTRACT

Optical analysis devices may be configured for optically interacting a material of interest with a chemical filter and a detector that together are configured to detect a characteristic of the material of interest, wherein optically interacting the material of interest with the chemical filter comprises absorbing, by the chemical filter, at least a portion of an electromagnetic radiation having optically interacted with the material of interest. Relative to dry cements, such optical analysis devices may be useful in classifying and/or grading dry cements and determining the composition and/or concentration of cement slurry additives to enhance the implementation efficacy of the dry cement.

20 Claims, 2 Drawing Sheets

(51) Int. Cl.
| | |
|---|---|
| C04B 40/00 | (2006.01) |
| C04B 28/32 | (2006.01) |
| C09K 8/46 | (2006.01) |
| C04B 28/04 | (2006.01) |
| C04B 28/14 | (2006.01) |
| C04B 28/34 | (2006.01) |
| C09K 8/42 | (2006.01) |
| G01N 21/27 | (2006.01) |
| G01N 33/38 | (2006.01) |

(52) U.S. Cl.
CPC .............. *C04B 28/14* (2013.01); *C04B 28/32* (2013.01); *C04B 28/34* (2013.01); *C09K 8/42* (2013.01); *C09K 8/46* (2013.01); *G01N 21/27* (2013.01); *G01N 33/383* (2013.01)

(58) Field of Classification Search
CPC ....... C09K 8/46; E21B 33/14; E21B 47/0005; E21B 47/102
See application file for complete search history.

(56) References Cited

U.S. PATENT DOCUMENTS

| | | |
|---|---|---|
| 8,237,920 B2 | 8/2012 | Jones et al. |
| 2009/0033933 A1 | 2/2009 | Myrick et al. |
| 2012/0132007 A1 | 5/2012 | Dria et al. |
| 2012/0205103 A1 | 8/2012 | Ravi et al. |
| 2014/0076549 A1 | 3/2014 | Pelletier et al. |

OTHER PUBLICATIONS

Dai, Bin, Simulations-Guided Design of Process Analytical Sensor Using Molecular Factor Computing, University of Kentucky Doctoral Dissertations, Paper 483, 2007.

Dai et al., Molecular Factor Computing for Predictive Spectroscopy, Pharmaceutical Research, 2007.

International Search Report and Written Opinion for PCT/US2014/052621 dated May 22, 2015.

Brooke et al., "Multimode Imaging in the Thermal Infrared for Chemical Contrast Enhancement. Part 1: Methodology," Anal. Chem. Oct. 2010, vol. 82, No. 20, pp. 8412-8420.

Brooke et al., "Multimode Imaging in the Thermal Infrared for Chemical Contrast Enhancement. Part 2: Simulation Driven Design," Anal. Chem. Oct. 2010, vol. 82, No. 20, pp. 8421-8426.

Brooke et al., "Multimode Imaging in the Thermal Infrared for Chemical Contrast Enhancement. Part 3: Visualizing Blood on Fabrics," Anal. Chem. Oct. 2010, vol. 82, No. 20, pp. 8427-8431.

SYSTEMS AND METHODS FOR ANALYZING THE CHARACTERISTICS AND COMPOSITIONS OF A DRY CEMENT

BACKGROUND

The exemplary embodiments described herein relate to systems and methods for analyzing a dry cement.

Set cement compositions are used in the oil and gas sector for many purposes including stabilizing wellbores and plugging wellbores. Set cements are produced from cement slurries that include water, dry cements, and optionally cement slurry additives. The operational parameters relating to the cement slurry and the characteristics of the resultant set cement are derived, at least in part, from the dry cement composition and the composition and concentration of the optional cement slurry additives.

Some types of dry cements (e.g., Portland cements) are classified and graded based on their composition. Dry cement classifications broadly characterize dry cements by the concentration of the major components (or analytes) in the dry cement. For example, the multitude of American Petroleum Institute ("API") classifications for Portland cements relate specifically to the relative concentration of four components $(CaO)_3.SiO_2$, $(CaO)_2.SiO_2$, $(CaO)_3.Al_2O_3$, and $(CaO)_3.Al_2O_3.Fe_2O_3$, whereas classifying Sorel cements may be based on the major components of MgO, $MgCl_2$, ZnO, $ZnCl_2$, and water.

Cement grades also relate to the composition of the dry cement, but to the minor components like metal compound concentration, sulfate concentration (e.g., sulfate salts), minor component oxide concentrations, and the like. The concentration of these minor components can affect the mechanical properties and setting chemistry of a set cement produced therefrom, which leads to variability within classifications of dry cements. For example, silicate minerals like $(CaO)_3.SiO_2$ may be used in grading a Sorel cement.

Classifying and grading a dry cement involves a complicated, multi-step process where harsh chemicals are mixed with the dry cement and then analyzed via expensive, time-consuming methods like x-ray diffraction and gravimetric analysis. Further, these classification and grading processes use equations and make assumptions that have been shown to introduce significant error into the analysis.

When the dry cement is incorrectly classified and graded, the incorrect composition and/or concentration of cement slurry additives may be used, resulting in an inefficient or ineffective cementing operation. In relation to downhole oil and gas operations, such cementing operations can increase both costs and the instances of remedial operations to repair the set cement.

BRIEF DESCRIPTION OF THE DRAWINGS

The following figures are included to illustrate certain aspects of the exemplary embodiments described herein, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
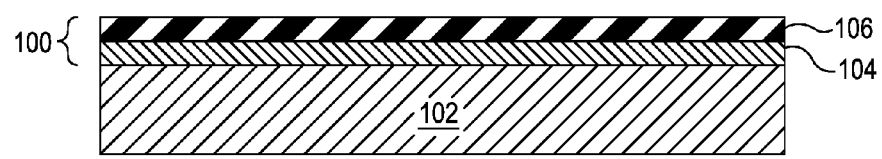
FIG. 1 illustrates an exemplary molecular factor computing element, according to one or more embodiments.

The exemplary embodiments described herein relate to optical analysis systems and methods that utilize molecular factor computing ("MFC") techniques in detecting and measuring the characteristics, including compositions, of a dry cement.

The exemplary systems and methods described herein employ various configurations of optical analysis devices, also commonly referred to as "opticoanalytical devices," that utilized MFC techniques for the rapid analysis of dry cements. The MFC techniques described herein utilize molecular absorbance filters calibrated to analyze at least one characteristic of a dry cement (e.g., the composition, concentration, or both, of individual components in the dry cement).

The disclosed systems and methods may be suitable for use in the oil and gas industry since the described optical analysis devices provide a cost-effective, rugged, and accurate means for classifying and grading dry cements in order to facilitate the effective production of cement slurries and set cements in oil/gas applications. It will be appreciated, however, that the various disclosed systems and methods are equally applicable to other technology fields including, but not limited to, the food and drug industry, industrial applications, mining industries, or any field where it may be advantageous to determine in real-time or near real-time a characteristic of a dry composition, especially to determine the quality of the dry composition.

As described above, the detailed analysis of the composition of dry cement currently requires extensive time, high cost, and harsh chemicals and can give unreliable results. By contrast, the optical analysis devices disclosed herein may provide rapid analysis of dry cements with minimal sample preparation, if any. Additionally, because the analysis is rapid, multiple measurements may be taken to reduce error. Further, because of the small size and relatively low cost of the optical analysis devices disclosed herein, the methods for analyzing dry cements presented herein may be suitable for not only laboratory use, but also, in-field analysis (e.g., at a manufacturing or mining site, at a distribution center, or at a well site).

A significant and distinct advantage of the optical analysis devices disclosed herein is that they can be configured to specifically detect and/or measure a particular characteristic of interest of a dry cement, thereby allowing qualitative and/or quantitative analyses of the material of interest to occur without having to undertake a time-consuming sample processing procedure. With rapid analyses capabilities on hand, the exemplary systems and methods described herein may be able to classify and/or grade dry cements, determine the composition and/or concentration of cement slurry additives to enhance the implementation efficacy of the dry cement, provide some measure of proactive or responsive control over the quality of the dry cement, allow for the collection and archival of information relating to the dry cement in conjunction with operational information to optimize subsequent operations, and any combination thereof.

As used herein, the term "dry cement" refers to a mixture of solid particles including at least some cement particles and is not hydrated beyond about ambient conditions (e.g., no additional water has been added). It should be noted that the term "dry cement" does not refer to set cements (e.g., that have been formed from a cement slurry).

Dry cements may comprise a single cement or comprise a blend of two or more cements. Examples of cements may include, but are not limited to, hydraulic cements, Portland cements, gypsum cements, pozzolan cements, calcium phosphate cements, high alumina content cements, silica cements, high alkalinity cements, shale cements, acid/base cements, magnesia cements (e.g., Sorel cements), zeolite cement systems, cement kiln dust cement systems, slag cements, micro-fine cements, bentonites, and the like, any derivative thereof, and any combination thereof. Examples of Portland cements may include, but are not limited to, Portland cements classified as Classes A, C, H, and G according to API and their equivalent, Ordinary Portland cements of Type I, I/II, III, and V according to ASTM, including combinations thereof. Examples of pozzolan cements may include, but are not limited to, fly ash, silica fume, granulated blast furnace slag, calcined shale, opaline shale, pumice, pumicite, diatomaceous earth, volcanic ash, tuft, cement kiln dust, and any combination thereof.

As used herein, the term "characteristic" refers to a chemical, mechanical, or physical property (quantitative or qualitative) of a material of interest (e.g., a dry cement or an analyte thereof). As used herein, the term "analyte" refers to a chemical component. The term analyte encompasses chemical components that are at least one of: present in the material of interest, may be added to the material of interest, involved in a chemical reaction (e.g., reagents and products) transpiring within the material of interest, and not involved in a chemical reaction transpiring within the material of interest. Illustrative characteristics of a material of interest that can be monitored with the optical analysis devices disclosed herein can include, for example, chemical composition (e.g., identity and concentration in total or of individual analytes), impurity content, pH, viscosity, density, ionic strength, total dissolved solids, salt content, porosity, opacity, bacteria content, particle size distribution, color, temperature, hydration level, oxidation state, and the like. Moreover, the phrase "characteristic of interest" may be used herein to refer to a characteristic of a material of interest.

Examples of analytes within a dry cement may include, but are not limited to, $SiO_2$, $Al_2O_3$, $FeO$, $Fe_2O_3$, $CaO$, $Na_2O$, $K_2O$, $MgO$, $SO_3$, $Mn_2O_3$, $TiO_2$, $P_2O_5$, $SnO$, $SrO$, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $SO_3$, $Ca(OH)_2$, $Al(OH)_4^-$, $H_4SiO_4$, free lime, inorganic salts (e.g., sodium, potassium, magnesium, and calcium salts of sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, water, and any combination thereof.

In some instances, the foregoing analytes may be used in classifying cements (i.e., as a major component) or as grading cements (i.e., as a minor component), which depends on the dry cement. As used herein, the "major component" of a dry cement refers to a component or analyte that identifies the type of dry cement (e.g., Portland cement versus Sorel cement or Type I Portland cement versus Type V Portland cement). As used herein, the "minor component" of a dry cement refers to a component or analyte that is not a major component. The terms "major component" and "minor component" do not necessarily relate to a concentration. For example, in Ordinary Grade, Class G Portland cement may have about 5% $(CaO)_3.Al_2O_3$ as one of the major components and up to about 6% MgO as one of the minor components.

As used herein, the term "cement slurry additive" refers to an additive that can be included in a cement slurry with water and a dry cement. Cement slurry additives may be liquids or dry additives (e.g., powders). In some instances, the dry cement and at least one cement slurry additive (typically a dry additive) may be combined to form a mixture that can be used in preparing a cement slurry. The mixture may be prepared at a storage facility, manufacturing facility, laboratory, distribution center, at the well site, or in transit between any of these locations.

Examples of cement slurry additives may include, but are not limited to, set retarders, set accelerators, fillers (e.g., weighting agents, lightweight particles like glass beads, rubber particles, and the like), dispersants, gelling agents, and the like, and any combination thereof.

As used herein, the term "electromagnetic radiation" refers to radio waves, microwave radiation, infrared and near-infrared radiation, visible light, ultraviolet light, X-ray radiation, and gamma ray radiation.

As used herein, the term "optical analysis device" refers to an optical device that is configured to receive an input of electromagnetic radiation from a substance or sample of the substance, produce output of electromagnetic radiation by interacting the input electromagnetic radiation with one or more chemical filters, and detect the output of electromagnetic radiation, which can be correlated to at least one characteristic of the substance being measured or monitored. The output of electromagnetic radiation from the one or more chemical filters can be reflected electromagnetic radiation, transmitted electromagnetic radiation, and/or dispersed electromagnetic radiation. Whether reflected or transmitted electromagnetic radiation is analyzed by the detector may be dictated by the structural parameters of the optical analysis device as well as other considerations known to those skilled in the art. In addition, emission and/or scattering by the substance, for example via fluorescence, luminescence, Raman scattering, and/or Rayleigh scattering, can also be monitored by the optical analysis devices.

As used herein, the term "optically interact" or variations thereof refers to the reflection, transmission, scattering, diffraction, or absorption of electromagnetic radiation either on, through, or from a specified material/component. Electromagnetic radiation may be optically interacted with a material of interest (e.g., a dry cement or analyte thereof), the chemical filters, the detector, and the like.

The exemplary systems and methods described herein will include at least one optical analysis device configured to measure at least one characteristic of a dry cement or analyte thereof. In some embodiments, the optical analysis devices suitable for use in the exemplary embodiments described herein may be mobile or portable. In some embodiments, the optical analysis devices suitable for use in the exemplary embodiments described herein may be a portion of tank, silo, vat, or the like that store, mix, or otherwise contain dry cement (e.g., in a wall).

In some instances, an optical analysis device may be configured for optically interacting a sample, at least one chemical filter, and a detector. For example, an optical analysis device may, in some instances, include an electromagnetic radiation source arranged to optically interact light with a material of interest, at least one chemical filter arranged to receive the optically interacted light from the material of interest, and at least one detector arranged to receive the optically interacted light from the at least one chemical filter. However, in at least one embodiment, the electromagnetic radiation source may be omitted and instead the electromagnetic radiation may be derived from the material of interest itself.

In some embodiments, the exemplary optical analysis devices may be specifically configured for detecting, analyzing, and quantitatively measuring a particular characteristic of the material of interest. In other embodiments, the optical analysis devices may be general purpose optical devices, with post-acquisition processing (e.g., through computer means) being used to specifically detect the characteristic of interest.

The presently described optical analysis devices combine the advantage of the power, precision, and accuracy associated with laboratory spectrometers, while being extremely rugged and suitable for field use. Furthermore, the optical analysis devices can be specifically configured to detect and analyze particular characteristics of interest. As a result, interfering signals are automatically discriminated from those of interest by appropriate selection of the chemical filters, such that the optical analysis devices provide a rapid response regarding the characteristic of interest as based on the output from the detector and little post-processing is required. In some embodiments, the output from the detector can be converted into the magnitude of the characteristic of interest (e.g., the concentration of an analyte). The foregoing advantages and others make the optical analysis devices particularly well suited for field use.

The optical analysis devices described herein utilize electromagnetic radiation to mimic calculations, as opposed to the hardwired circuits of conventional electronic processors. For example, when electromagnetic radiation interacts with a material of interest, unique physical and chemical information about the material of interest may be encoded in the electromagnetic radiation that is reflected from, transmitted through, or radiated from the material of interest. This information is often referred to as the spectral "fingerprint" of the material of interest. The optical analysis devices described herein are capable of extracting the information of the spectral fingerprint of multiple characteristics of a material of interest (e.g., a dry cement blend or an analyte thereof), and converting that information into a detectable output regarding the overall properties of the monitored material of interest. That is, through suitable configurations of the optical analysis devices, electromagnetic radiation associated with characteristics of interest can be separated from electromagnetic radiation associated with all other components of the material of interest in order to estimate the properties (e.g., chemical compositions, analyte concentration, and the like) of the monitored substance (e.g., a dry cement blend or an analyte thereof) in real-time or near real-time.

The chemical filters described herein are generally a series of thin films that are deposited on a substrate. In some instances, the chemical filter may be deposited directly on the detector. In some instances, the chemical filter may be deposited on an optically transparent substrate (e.g., an IR-transparent substrate), which may be placed between the material of interest and the detector.

The chemical filters used in the exemplary optical analysis devices described herein selectively reduce the detector's sensitivity to wavelengths absorbed by the chemical filter. The pattern of the electromagnetic radiation intensities measured by the detector is similar to a mini-spectrum that contains only a few spectrally-convoluted measurements that are used as a basis for analysis. The chemical filters may be designed to either absorb the electromagnetic radiation having optically interacted with the material of interest or absorb the background electromagnetic radiation.

Referring to FIG. 1, illustrated is an exemplary chemical filter 100 deposited on a detector 102 suitable for use in the optical analysis devices used in the systems and methods described herein. The chemical filter 100 includes a reflecting layer 104 between a sensing layer 106 and the detector 102.

The sensing layer 106 may enhance the sensitivity or selectivity of the detector. The sensing layer 106 may be formed by a thin film or series of thin films (e.g., thin films of polymers, complex organic molecules, semiconductors, and the like, in any combination) where the thickness and composition of each thin film are used to produce a desired absorption characteristic. One of skill in the art would recognize the available techniques for designing and producing the sensing layer 106 of the chemical filter 100. For example, computer programs are available for designing the thickness and composition of the thin film or the series of thin films. Additionally, techniques like dip coating, sputter coating, and the like may be used for forming the thin films.

Accordingly, sensing layer 106 is configured to absorb at least a portion of an electromagnetic radiation interacting with chemical filter 100. In that regard, the electromagnetic radiation interacting with chemical filter 100 may be an electromagnetic radiation previously interacted with the sample (e.g., the dry cement). Moreover, sensing layer 106 may include a plurality of absorbing layers. Each absorbing layer in sensing layer 106 may be configured to absorb a different portion of the electromagnetic radiation interacted with the sample. For example, in some embodiments the accumulated absorption profiles of the plurality of absorbing layers forming sensing layer 106 may return an optical signal (i.e., absorption or transmission) of the sample when chemical filter 100 is interacted with an electromagnetic radiation. The thickness of each of the absorbing layers forming sensing layer 106 may be determined according to an optical thickness desired for sensing layer 106 in a portion of the spectrum of the electromagnetic radiation. The optical thickness desired for sensing layer 106 in a portion of the spectrum determines the amount of electromagnetic radiation absorbed and transmitted by chemical filter 100 in the portion of the spectrum. Thus, the number of absorbing layers, the material, and the thickness of each of the absorbing layers result in an optical signal proportional to the characteristic of interest of the sample.

The reflecting layer 104 may act as an infrared mirror by reflecting wavelengths of non-interest. Gold, silver, and other interference coatings may be used to form the reflective layer 104. The reflective layer 104 may also enhance the thermal response of the detector 102 to wavelengths of interest.

In some instances, an absorbing layer may be used as an alternative to the reflecting layer 104, where the absorbing layer absorbs the wavelengths of non-interest.

In some instances, an insulating layer (not shown) may be included between the detector 102 and the chemical filter 100. The insulating layer may be deposited on the detector 102 before deposition of the various layers of the chemical filter 100, so as to prevent the detector 102 from shorting out during addition of the various layers of the chemical filter 100.

Detectors 102 suitable for use in conjunction with the optical analysis devices described herein may be thermal or charge coupled devices. Exemplary thermal devices may include thermocouples, thermopile arrays (thermocouples connected in series or parallel), bolometer detectors or microbolometer detectors (an array of pixels that measure a change in electrical resistance that occurs as a result of temperature change), and pyroelectric detectors (non-centrosymmetric crystalline materials that contain a dipole unit cell).

In embodiments where detector 102 is a thermal detector, reflecting layer 104 is configured to optically decouple detector 102 from the electromagnetic radiation interacted with the sample. Reflecting layer 104 may be formed of a material that thermally couples sensing layer 106 and detector 102. Accordingly, reflecting layer 104 may be configured to allow thermal energy to be transferred between sensing layer 106 and detector 102. Absorption of a portion of the electromagnetic radiation interacted with the sample in sensing layer 106 results in the heating of sensing layer 106. The heat of sensing layer 106 is transferred to and measured by thermal detector 102, thereby providing a signal indicative of the portion of the electromagnetic radiation interacted with the sample. When the electromagnetic radiation interacted with the sample is modulated at a certain frequency, fs, a thermal thickness, Tfs, above detector 102 defines the portion of chemical sensor 100 that is thermally coupled with detector 102. Material layers located at a distance from detector 102 greater than Tfs may not be thermally coupled to detector 102. In some embodiments, Tfs varies inversely with frequency, fs. That is, a higher fs may result in a lower Tfs, according to some embodiments. Thus, by adjusting different values of fs, some embodiments are capable of determining an optical response of chemical sensor 100 for each of a plurality of layers forming sensing layer 106.

As described above, in alternative embodiments, the detector 102 may be replaced with an optically transparent substrate to produce a chemical filter 100 that may be separate from the detector 102.

Figure 2:
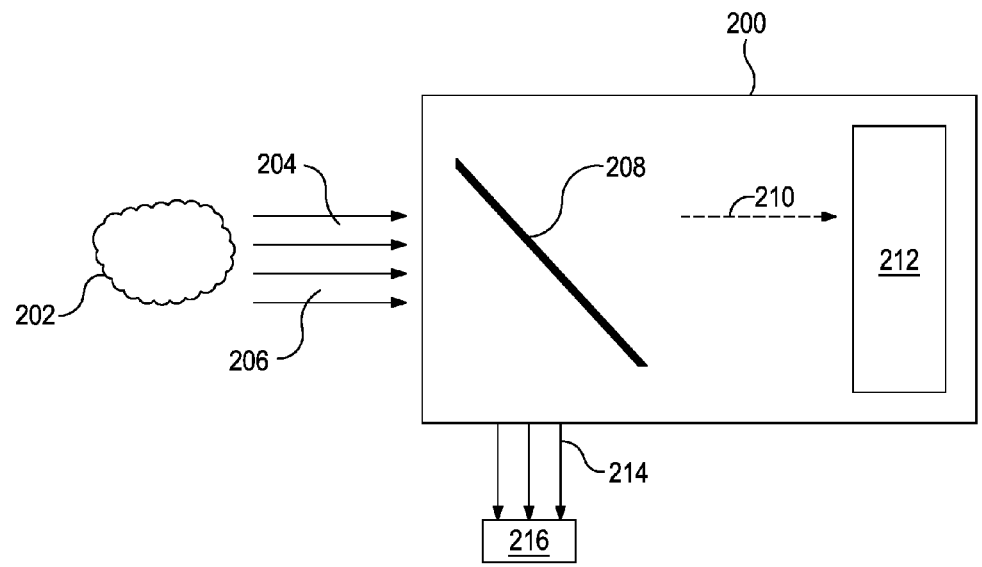
FIG. 2 illustrates a block diagram non-mechanistically illustrating how an optical analysis device distinguishes electromagnetic radiation related to a characteristic of interest from other electromagnetic radiation, according to one or more embodiments.

Referring now to FIG. 2, illustrated is a block diagram that non-mechanistically illustrates how an optical analysis device 200 is able to distinguish electromagnetic radiation related to a characteristic of interest from other electromagnetic radiation. As shown in FIG. 2, after being illuminated with incident electromagnetic radiation, a dry cement 202 produces an output of electromagnetic radiation (e.g., sample-interacted light), some of which is electromagnetic radiation 204 corresponding to the characteristic of interest and some of which is background electromagnetic radiation 206 corresponding to other characteristics of the dry cement 202. In some embodiments, the dry cement 202 may include one or more characteristics of interest that may correspond to the one or more analytes of the dry cement 202.

Although not specifically shown, one or more conventional filters may be employed in the optical analysis device 200 in order to restrict the optical wavelengths and/or bandwidths of the system and thereby eliminate unwanted electromagnetic radiation existing in wavelength regions that have no importance. Such filters can be located anywhere along the optical train, but are typically employed directly after a light source, which provides the initial electromagnetic radiation.

The beams of electromagnetic radiation 204, 206 impinge upon the optical analysis device 200, which contains an exemplary chemical filter 208 therein. In the illustrated embodiment, the chemical filter 208 may be configured to produce optically interacted light, for example, transmitted optically interacted light 210 and reflected optically interacted light 214 (e.g., where the chemical filter 208 includes a reflecting layer described relative to FIG. 1). In operation, the chemical filter 208 may be configured to distinguish the electromagnetic radiation 204 from the background electromagnetic radiation 206 as described relative to FIG. 1.

The transmitted optically interacted light 210, which may be related to the characteristic of interest of the dry cement 202, may be conveyed to a detector 212 for analysis and quantification. As illustrated, the chemical filter 208 may be separate from the detector 212.

In embodiments where detector 212 is a thermal detector, chemical filter 208 may be thermally coupled to the sensitive area of detector 212. For example, in some embodiments chemical filter 208 includes a sensing layer adjacent to detector 212 (e.g., chemical filter 100, cf. FIG. 1).

In some embodiments, the detector 212 is configured to produce an output signal in the form of a voltage that corresponds to the particular characteristic of the dry cement 202. In at least one embodiment, the signal produced by the detector 212 and the characteristic of a dry cement 202 (e.g., concentration of an analyte) may be directly proportional. In other embodiments, the relationship may be a polynomial function, an exponential function, and/or a logarithmic function. The reflected optically interacted light 214, which may be related to other characteristics of the dry cement 202, can be directed away from detector 212. In alternative configurations, the chemical filter 208 may be configured such that the reflected optically interacted light 214 can be related to the characteristic of interest, and the transmitted optically interacted light 210 can be related to other characteristics in the dry cement 202. In alternative configuration, the chemical filter 208 may include an absorbing layer rather than a reflecting layer, thereby absorbing the optically interacted light corresponding to the background such that the transmitted optically interacted light 210 is related to other characteristics of the dry cement 202.

In some embodiments, a second detector 216 can be present and arranged to detect the reflected optically interacted light 214. In other embodiments, the second detector 216 may be arranged to detect the electromagnetic radiation 204, 206 derived from the dry cement 202 or electromagnetic radiation directed toward or before the dry cement 202. Without limitation, the second detector 216 may be used to detect radiating deviations stemming from an electromagnetic radiation source (not shown), which provides the electromagnetic radiation (i.e., light) to the device 200. For example, radiating deviations can include such things as, but not limited to, intensity fluctuations in the electromagnetic radiation, interferent fluctuations (e.g., dust or other interferents passing in front of the electromagnetic radiation source), coatings on windows included with the optical analysis device 200, combinations thereof, or the like. In some embodiments, a beam splitter (not shown) can be employed to split the electromagnetic radiation 204, 206, and the transmitted or reflected electromagnetic radiation can then be directed to two or more chemical filters 208. That is, in such embodiments, the chemical filter 208 does not function as a type of beam splitter, as depicted in FIG. 2, and the transmitted or reflected electromagnetic radiation simply passes through the chemical filter 208, being optically interacted therein, before travelling to the detector 212.

The characteristic(s) of interest being analyzed using the optical analysis device 200 can be further processed and/or analyzed computationally to provide additional characterization information about the dry cement 202 or an analyte thereof. In some embodiments, the identification and concentration of each analyte of interest in the dry cement 202 can be used to predict certain physical characteristics of the dry cement 202. For example, the bulk characteristics of the dry cement 202 (e.g., reactivity, set time, and the like) can be estimated by using a combination of the properties conferred to the dry cement 202 by each analyte. For example, the relative ratios of some of the analytes can indicate the concentration or range of concentration of cement slurry additives that should be used in preparing a cement slurry from the dry cement.

In some embodiments, the magnitude of the characteristic of interest determined using the optical analysis device 200 can be fed into an algorithm operating under computer control. The algorithm may be configured to make predictions on how the characteristics of the dry cement 202 would change if the magnitude of the characteristic of interest is changed relative to one another. In some embodiments, the algorithm can produce an output that is readable by an operator who can manually take appropriate action, if needed, based upon the reported output. In other embodiments, however, the algorithm can take proactive process control. For example, in the production of some cements, the particles are heated in a kiln. Periodically monitoring the composition and concentration of analytes in the dry cement in the kiln may allow for changing the temperature of the kiln or length of time the dry cement is in the kiln to achieve a desired classification or grade of dry cement. In another example, in storage, the composition and concentration of analytes can be analyzed for a reduction in the quality of the dry cement. In some instances, the stored dry cement may be mixed with other dry cement to achieve a desired classification or grade of dry cement. By way of nonlimiting example, lime can degrade over time with exposure to carbon dioxide and, accordingly, may be an analyte of interest to analyze by such methods.

The algorithm can be part of an artificial neural network configured to use the concentration of each characteristic of interest in order to evaluate the overall characteristic(s) of the dry cement 202 and predict the composition and/or concentration of the cement slurry additives to be included to provide for desired properties in a resultant cement slurry. It is to be recognized that an artificial neural network can be trained using samples of predetermined characteristics of interest, and thereby generating a virtual library. As the virtual library available to the artificial neural network becomes larger, the neural network can become more capable of accurately predicting the characteristic of interest corresponding to a dry cement or analyte thereof. Furthermore, with sufficient training, the artificial neural network can more accurately predict the characteristics of the dry cement, even in the presence of unknown analytes.

In some embodiments, the data collected using the optical analysis devices can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a chemical reaction process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site (e.g., via wireless technology).

Figure 3:
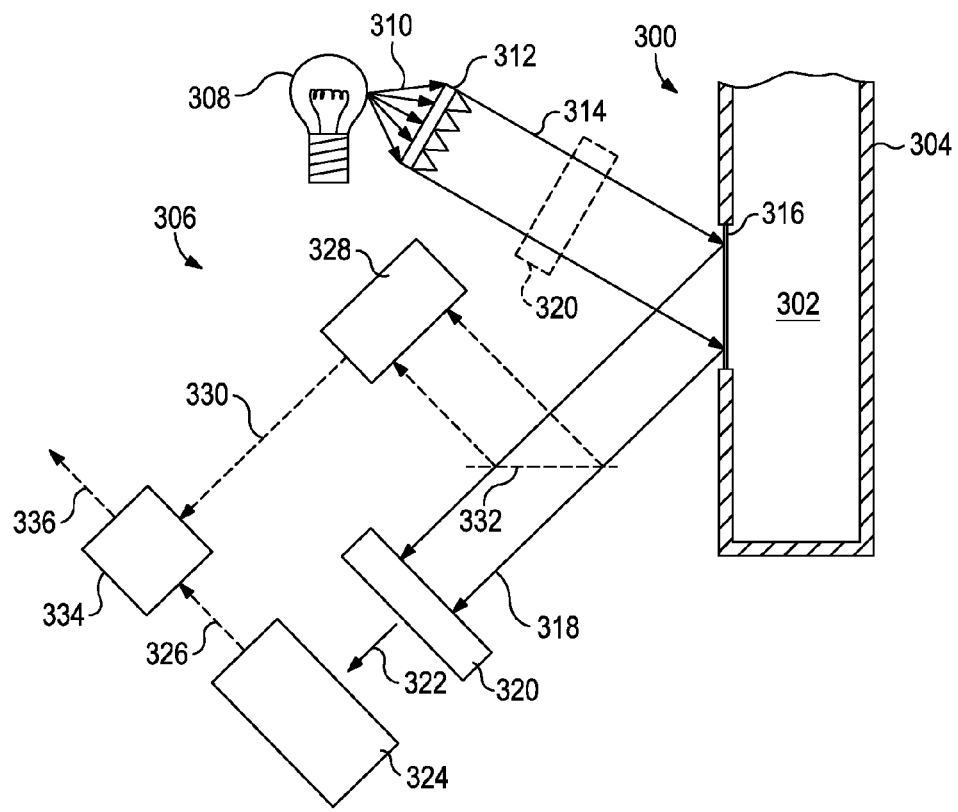
FIG. 3 illustrates an exemplary system for monitoring a dry cement present in a container, according to one or more embodiments.

Referring now to FIG. 3, illustrated is an exemplary system 300 for monitoring a dry cement 302, according to one or more embodiments. In the illustrated embodiment, the dry cement 302 may be contained within an exemplary container 304. In at least one embodiment, the container 304 may be a mixer and the dry cement 302 present therein may be actively mixing while measurements are being taken. In at least one embodiment, the container 304 may be a cup or the like of a mobile device. As will be appreciated, however, in other embodiments the container 304 may be any other type of container, as generally described or otherwise defined herein. For example, the container 304 may be a storage vessel or silo.

The system 300 may include at least one optical analysis device 306, which may be similar in some respects to the optical analysis device 200 of FIG. 2, and therefore may be best understood with reference thereto. While not shown, the device 306 may be housed within a casing or housing configured to substantially protect the internal components of the device 306 from damage or contamination from the external environment. The housing may operate to mechanically couple the device 306 to the container 304 with, for example, mechanical fasteners, brazing or welding techniques, adhesives, magnets, combinations thereof or the like.

As described in greater detail below, the optical analysis device 306 may be useful in determining a particular characteristic of the dry cement 302 within the container 304, such as determining a concentration of an analyte present within the dry cement 302.

Knowing at least some of the characteristics of the dry cement 302 may help determine the overall composition of the dry cement 302. Knowing the composition of the dry cement 302 allows for a more accurate determination of the composition and/or concentration of cement slurry additives to use in a subsequent cement slurry. In turn, the cementing operation that utilized the cement slurry may be more effective as premature setting or delayed setting may be mitigated. Further, the resultant set cement may be of higher quality because the type of and concentration of additives was tailored to the original dry cement.

In some embodiments, the device 306 may include an electromagnetic radiation source 308 (e.g., a broadband light source) configured to emit or otherwise generate electromagnetic radiation 310. The electromagnetic radiation source 308 may be any device capable of emitting or generating electromagnetic radiation, as defined herein. For example, the electromagnetic radiation source 308 may be a light bulb, a light emitting device (LED), a laser, a blackbody, a photonic crystal, an X-Ray source, combinations thereof, or the like. In some instances, the electromagnetic radiation source 308 may be modulated such that the frequency of electromagnetic radiation incident on the sample, fs, changes. This may be achieved with a filter wheel, an optical chopper, optical choppers, and the like. Accordingly, in some embodiments different values of fs may be used during a measurement cycle. Moreover, in some embodiments the value of fs may be adjusted continuously in order to collect signals from different sensing layers in a chemical filter 320. By changing the modulation frequency, fs, the thermal diffusion length, Ts, is also changed.

Ts determines the amount of time the electromagnetic radiation spends in a particular layer; therefore, by modifying or adjusting fs accordingly, one can effectively activate or deactivate different sensing layers. For example, the fs could be chosen to make all layers thermally thin. In this case, all layers would be inside of Ts and the detected optical signal would be the result of absorption by all layers. In yet another example, fs could be selected so that only the sensing layers close to the detector are thermally thin and all other layers are outside of Ts. The detected optical signal in this example would be the result of absorption in only those layers close to the detector or inside of Ts. In some embodiments, a lens 312 may be configured to collect or otherwise receive the electromagnetic radiation 310 and direct a beam 314 of electromagnetic radiation 310 toward the dry cement 302. The lens 312 may be any type of optical device configured to transmit or otherwise convey the electromagnetic radiation 310 as desired. For example, the lens 312 may be a normal lens, a Fresnel lens, a diffractive optical element, a holographic graphical element, a mirror (e.g., a focusing mirror), a type of collimator, or any other electromagnetic radiation transmitting device known to those skilled in art. In other embodiments, the lens 312 may be omitted from the device 306 and the electromagnetic radiation 310 may instead be conveyed toward the dry cement 302 directly from the electromagnetic radiation source 308.

In one or more embodiments, the device 306 may also include a sampling window 316 arranged adjacent to or otherwise in contact with the dry cement 302 for detection purposes. The sampling window 316 may be made from a variety of transparent, rigid or semi-rigid materials that are configured to allow transmission of the electromagnetic radiation 310 therethrough. For example, the sampling window 316 may be made of, but is not limited to, glasses, plastics, semi-conductors, crystalline materials, polycrystalline materials, hot or cold-pressed powders, combinations thereof, or the like.

After passing through the sampling window 316, the electromagnetic radiation 310 impinges upon and optically interacts with the dry cement 302, including any analytes present within the dry cement 302. As a result, optically interacted radiation 318 is generated by and reflected from the dry cement 302. Those skilled in the art, however, will readily recognize that alternative variations of the device 306 may allow the optically interacted radiation 318 to be generated by being transmitted, scattered, diffracted, absorbed, emitted, or re-radiated by and/or from the dry cement 302, or one or more analytes present within the dry cement 302, without departing from the scope of the disclosure.

The optically interacted radiation 318 generated by the interaction with the dry cement 302 may be directed to or otherwise received by a chemical filter 320 arranged within the device 306. In operation the chemical filter 320 may be configured to receive the optically interacted radiation 318 and produce modified electromagnetic radiation 322 corresponding to a particular characteristic of interest of the dry cement 302. In particular, the modified electromagnetic radiation 322 is electromagnetic radiation that has optically interacted with the chemical filter 320, whereby an approximate mimicking of the absorption spectrum corresponding to the characteristic of interest is obtained. In some embodiments, the characteristic of interest corresponds to the dry cement 302. In other embodiments, the characteristic of interest corresponds to a particular analyte found in the dry cement 302.

It should be noted that, while FIG. 3 depicts the chemical filter 320 as receiving optically interacted radiation 318 from the dry cement 302, the chemical filter 320 may be arranged at any point along the optical train of the device 306, without departing from the scope of the disclosure. For example, in one or more embodiments, the chemical filter 320 (as shown in dashed) may be arranged within the optical train prior to the sampling window 316 and equally obtain substantially the same results. In other embodiments, the sampling window 316 may serve a dual purpose as both a transmission window and the chemical filter 320 (i.e., a spectral component). In yet other embodiments, the chemical filter 320 may generate the modified electromagnetic radiation 322 through reflection, instead of transmission therethrough. In further embodiments, chemical filter 320 may include a sensing layer disposed adjacent to a thermal detector (e.g., chemical filter 100 and detector 102, cf. FIG. 1), the sensing layer modifying an electromagnetic radiation optically interacted with dry cement 302.

Moreover, while only one chemical filter 320 is shown in the device 306, embodiments are contemplated herein which include the use of at least two chemical filters 320 or components thereof in the device 306 configured to cooperatively determine the characteristic of interest in the dry cement 302. For example, two or more chemical filters 320 may be arranged in series or parallel within the device 306 and configured to receive the optically interacted radiation 318 and thereby enhance sensitivities and detector limits of the device 306. In other embodiments, two or more chemical filters 320 may be arranged on a movable assembly, such as a rotating disc or an oscillating linear array, which moves such that the individual chemical filter 320 or components thereof are able to be exposed to or otherwise optically interact with electromagnetic radiation 310 for a distinct brief period of time. The two or more chemical filters 320 or components thereof in any of these embodiments may be configured to be either associated or disassociated with the characteristic of interest in the dry cement 302. In some embodiments, it may be desirable to monitor more than one characteristic of interest at a time using the device 306. In such embodiments, various configurations for multiple chemical filters 320 can be used, where each chemical filter 320 is configured to detect a particular and/or distinct characteristic of interest corresponding, for example, to the dry cement 302 or an analyte in the dry cement 302. In some embodiments, the characteristic of interest can be analyzed sequentially using multiple chemical filters 320 that are provided a single beam of optically interacted radiation 318 being reflected from or transmitted through the dry cement 302. In some embodiments, as briefly mentioned above, multiple chemical filters 320 can be arranged on a rotating disc, where the individual chemical filters 320 are only exposed to the beam of optically interacted radiation 318 for a short time. Advantages of this approach can include the ability to analyze multiple characteristics of interest within the dry cement 302 using a single device 306 and the opportunity to assay additional characteristics simply by adding additional chemical filters 320 to the rotating disc corresponding to those additional characteristics.

In other embodiments, multiple devices 306 can be placed at a single location along the container 304, where each device 306 contains a unique chemical filter 320 that is configured to detect a particular characteristic of interest. In such embodiments, a beam splitter can divert a portion of the optically interacted radiation 318 being reflected by, emitted from, or transmitted through the dry cement 302 and into each device 306. Each device 306, in turn, can be coupled to a corresponding detector (e.g., detector 324) or detector array that is configured to detect and analyze an output of electromagnetic radiation from the respective optical analysis device. Parallel configurations of optical analysis devices can be particularly beneficial for applications that require low power inputs and/or no moving parts.

Those skilled in the art will appreciate that any of the foregoing configurations can further be used in combination with a series configuration in any of the present embodiments. For example, two devices 306 may be arranged in series, such as being located on or within a movable housing configured to perform an analysis at a single location in the container 304. Likewise, multiple detection stations, each containing devices 306 in parallel, can be placed in series for performing a similar analysis.

The modified electromagnetic radiation 322 generated by the chemical filter 320 may subsequently be conveyed to a detector 324 for quantification of the signal. The detector 324 may be any device capable of detecting electromagnetic radiation, and may be generally characterized as an optical transducer. In some embodiments, the detector 324 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 324 may be configured to produce an output signal 326 in real-time or near real-time in the form of a voltage (or current) that corresponds to the particular characteristic of interest in the dry cement 302. The voltage returned by the detector 324 is essentially the dot product of the optical interaction of the optically interacted radiation 318 with the respective chemical filter 320 as a function of the concentration of the characteristic of interest. As such, the output signal 326 produced by the detector 324 and the concentration of the characteristic of interest may be related, for example, directly proportional. In other embodiments, however, the relationship may correspond to a polynomial function, an exponential function, a logarithmic function, and/or a combination thereof.

In some embodiments, the device 306 may include a second detector 328 which may be similar to the first detector 324 in that it may be any device capable of detecting electromagnetic radiation. Similar to the second detector 216 of FIG. 2, the second detector 328 of FIG. 3 may be used to detect radiating deviations stemming from the electromagnetic radiation source 308.

Undesirable radiating deviations can occur in the intensity of the electromagnetic radiation 310 due to a wide variety of reasons and potentially causing various negative effects on the output of the device 306. These negative effects can be particularly detrimental for measurements taken over a period of time. In some embodiments, radiating deviations can occur as a result of a build-up of film or material on the sampling window 316 which has the effect of reducing the amount and quality of light ultimately reaching the first detector 324. Without proper compensation, such radiating deviations could result in false readings and the output signal 326 would no longer be primarily or accurately related to the characteristic of interest.

To compensate for these types of undesirable effects, the second detector 328 may be configured to generate a compensating signal 330 generally indicative of the radiating deviations of the electromagnetic radiation source 308, and thereby normalize the output signal 326 generated by the first detector 324. As illustrated, the second detector 328 may be configured to receive a portion of the optically interacted radiation 318 via a beam splitter 332 in order to detect the radiating deviations. In other embodiments, however, the second detector 328 may be arranged to receive electromagnetic radiation from any portion of the optical train in the device 306 in order to detect the radiating deviations, without departing from the scope of the disclosure.

In some applications, the output signal 326 and the compensating signal 330 may be conveyed to or otherwise received by a signal processor 334 communicably coupled to both the detectors 324,328. The signal processor 334 may be a computer including a non-transitory machine-readable medium, and may be configured to computationally combine the compensating signal 330 with the output signal 326 in order to normalize the output signal 326 in view of any radiating deviations detected by the second detector 328. In some embodiments, computationally combining the output and compensating signals 326,330 may entail computing a ratio of the two signals 326,330. For example, the concentration or magnitude of each characteristic of interest determined using the optical analysis device 306 can be fed into an algorithm run by the signal processor 334. The algorithm may be configured to make predictions on how the dry cement 302 in combination with cement slurry additives, optionally at varying concentrations, will behave in a cement slurry.

In real-time or near real-time, the signal processor 334 may be configured to provide a resulting output signal 336 corresponding to the characteristic of interest. In some embodiments, as briefly discussed above, the resulting output signal 336 may be readable by an operator who can consider the results and take appropriate action, if needed, based upon the magnitude of the measured characteristic of interest. In some embodiments, the resulting output signal 336 may be conveyed, either wired or wirelessly, to the user for consideration.

Systems similar to that illustrated in FIG. 3 may be useful in analyzing dry cements. For example, a system may include a probe that can be inserted into a dry cement for analysis of a characteristic thereof. As such, the dry cement may be contained within a container not having a device 306 connected thereto (e.g., a bag of dry cement as shipped from a distributor). Further, the dry cement may not be contained within a container, but rather may be a pile or mound of dry cement.

Figure 4:
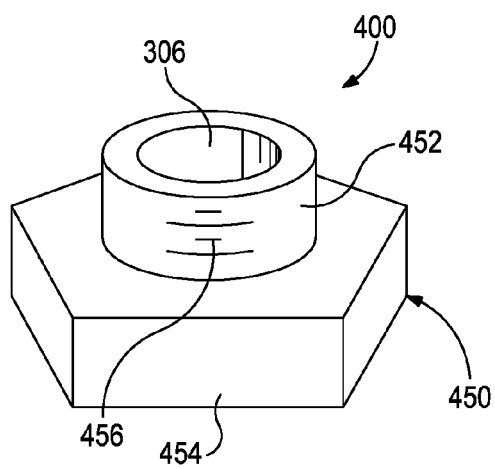
FIG. 4 illustrates an exemplary housing that may be used to house an optical analysis device, according to one or more embodiments.

Referring now to FIG. 4, with continued reference to FIG. 3, illustrated is an exemplary housing 400 that may be used to house an optical analysis device, according to one or more embodiments. In some embodiments, the housing 400 may be mechanically coupled to the container 304 using, for example, mechanical fasteners, brazing or welding techniques, adhesives, magnets, combinations thereof or the like. The housing 400 may be configured to substantially protect the internal components of the respective device 306 from damage or contamination from the external environment. Those skilled in the art, however, will readily recognize that several alternative designs and configurations of housings used to house the optical analysis devices are suitable for the presently disclosed systems and methods. Indeed, the housing embodiments described and disclosed herein are by way of example only, and should not be considered limiting to the exemplary systems and methods disclosed herein.

As illustrated, the housing 400 may be in the general form of a bolt 450 which encloses the various components of an optical analysis device, such as the device 306 of FIG. 3. In one embodiment, the components of the device 306 housed within the housing 400 may be generally housed within a stem 452 of the bolt 450, and the bolt 450 may have a hex head 454 for manual manipulation of the housing 400 using, for example, a wrench or other suitable torque-generating hand tool.

In at least one embodiment, the housing 400 defines external threads 456 that are threadable with corresponding mating pipe threads provided in, for example, an opening defined in the container 304 (FIG. 3) that is configured to receive the housing 400. The threads 456 may be sealed to the mating pipe threads with a thread sealant. The sampling window 316 is configured to be in optical communication with the dry cement 302 (FIG. 3) and allows optical interaction between the dry cement 302 and the other internal components of the internally-housed device 306.

Referring again to FIG. 3, those skilled in the art will readily recognize that, in one or more embodiments, electromagnetic radiation may be derived from the dry cement 302 itself, and otherwise derived independent of the electromagnetic radiation source 308. For example, various substances naturally radiate electromagnetic radiation that is able to optically interact with the chemical filter 320. In some embodiments, for example, the dry cement 302 or the substance within the dry cement 302 may be a blackbody radiating substance configured to radiate heat that may optically interact with the chemical filter 320. In other embodiments, the dry cement 302 or the substance within the dry cement 302 may be radioactive or chemo-luminescent and, therefore, radiate electromagnetic radiation that is able to optically interact with the chemical filter 320. In yet other embodiments, the electromagnetic radiation may be induced from the dry cement 302 or the substance within the dry cement 302 by being acted upon mechanically, magnetically, electrically, combinations thereof, or the like. For instance, in at least one embodiment, a voltage may be placed across the dry cement 302 or the substance within the dry cement 302 in order to induce the electromagnetic radiation. As a result, embodiments are contemplated herein where the electromagnetic radiation source 308 is omitted from the particular optical analysis device.

The optical analysis device described herein may be implemented for classifying and/or grading dry cement based on each of the characteristics of the dry cement. For example, a dry cement may be optically interacted with at least one chemical filter described herein and at least one detector described herein. The chemical filters/detectors may be configured to detect at least one characteristic of interest of the dry cement. The detector may then generate an output signal corresponding to each of the characteristics of the dry cement. At least one signal processor may then receive and process the output signals to produce a value for each of the characteristics measured and analyzed. These values may then be used to classify, grade, or both, the dry cement.

For example, in some instances for classifying Portland cements, gypsum cements, and some hydraulic cements, the characteristic of the dry cement may be at least one selected from the group of a concentration of $(CaO)_3.SiO_2$, a concentration of $(CaO)_2.SiO_2$, a concentration of $(CaO)_3.Al_2O_3$, a concentration of $(CaO)_3.Al_2O_3.Fe_2O_3$, and any combination thereof. In another example, in some instances for classifying, the characteristic of the dry cement may be a relative concentration ratio of at least two selected from the group of $(CaO)_3.SiO_2$, $(CaO)_2.SiO_2$, $(CaO)_3.Al_2O_3$, and $(CaO)_3.Al_2O_3.Fe_2O_3$.

In yet another example, in some instances for classifying Sorel cements, the characteristic of the dry cement may be at least one selected from the group of a concentration of MgO, a concentration of $MgCl_2$, a concentration of ZnO, a concentration of $ZnCl_2$, a concentration of water, and any combination thereof. In another example, in some instances for classifying Sorel cements, the characteristic of the dry cement may be a relative concentration ratio of at least two selected from the group of MgO, $MgCl_2$, ZnO, $ZnCl_2$, and water.

In yet another example, in some instances for classifying calcium phosphate cements, the characteristic of the dry cement may be at least one selected from the group of a concentration of CaO, a concentration of phosphate, a concentration of hydroxide, a concentration of water, and any combination thereof. In another example, in some instances for classifying calcium phosphate cements, the characteristic of the dry cement may be a relative concentration ratio of CaO to phosphate. Further, in some instances for classifying, the characteristic of the dry cement may be a relative concentration ratio of water to hydroxide.

One of ordinary skill in the art will recognize the major components that should be analyzed for the various examples of dry cements.

In yet another example, in some instances for grading, the characteristic of the dry cement may be a concentration of at least one selected from the group of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $SO_3$, $Ca(OH)_2$, $Al(OH)_4^-$, $H_4SiO_4$, free lime, inorganic salts (e.g., sodium, potassium, magnesium, and calcium salts of sulfate, phosphate, and carbonate), metal containing compounds (e.g., bromide, chloride, nitrate, sulfate, and phosphate salts of cadmium, zinc, nickel, copper, lead, and the like, metal oxides of such metals, and the like), hydroxides, water, and any combination thereof.

In some instances, reporting the classification and grade of the dry cement may be according to API or ASTM classifications/grades. In some instances, reporting the classification and grade of the dry cement may be a listing of at least some of the analytes in the dry cement and their respective concentration and/or relative ratios.

In another exemplary method, a concentration and/or a composition of a cement slurry additive to be used in conjunction with the dry cement may be determined based on the value for each of the characteristics measured and analyzed by the optical analysis device (e.g., a concentration of at least one analyte, a relative ratio of two or more analytes, the presence or absences of an analyte, or particle size distribution of the particles in the dry cement). In some instances, determining the concentration and/or the composition of the cement slurry additive may use computers and optionally artificial neural networks.

In some instances, it may not be necessary to explicitly classify or grade the dry cement to determine a concentration and/or a composition of a cement slurry additive to be used in conjunction with the dry cement.

One skilled in the art would understand the appropriate concentration and/or composition of a cement slurry additive based on the composition of analytes and their relative ratios present in the dry cement. For example, dry cements that comprise more free lime may benefit from a higher concentration of set retarder additives. In another example, dry cements that comprise higher concentrations of copper and/or zinc may benefit from additives to enhance the compressive strength of the resultant set cement. In yet another example, the level of sulfate (e.g., sulfate salts) or another suitable additive may be adjusted in response to the concentration of $(CaO)_3.Al_2O_3$ to enhance fluidity. In another example, the concentration of $K_2O$ and $Na_2O$ in the dry cement effect the reactivity of $(CaO)_3.Al_2O_3$. Specifically, $K_2O$ increases the activity of $(CaO)_3.Al_2O_3$ while $Na_2O$ decreases the activity. Sulfate (e.g., sulfate salts) and other additives may be added in appropriate concentration to counteract both oxides. In yet another example, high levels of free CaO and MgO can result in too much expansion in the set cement, which can be an avenue to failure of the set cement. Addition of sodium chloride, magnesium chloride, calcium chloride, calcium fluoride, and other additives may be added to the dry cement (during or after manufacturing of the dry cement) to address this issue. In another example, particle size may be useful in determining a composition or concentration of cement slurry additive to be used. For example, larger particle sizes that can lead to a reduced strength set cement may benefit from a strengthening cement slurry additive (e.g., fibers or other resilient particles). In another example, small particle sizes may benefit from more water to completely hydrate because of the increased surface area.

In some instances, after determining a concentration and/or a composition of a cement slurry additive as described herein, a mixture comprising the dry cement and the cement slurry additive may be mixed or otherwise prepared. Then, the mixture may be used in a wellbore operation (e.g., a primary cementing operation, a secondary cementing operation, or a remedial cementing operation).

In some instances, after determining a concentration and/or a composition of a cement slurry additive as described herein, a kit comprising the dry cement and an additive composition and concentration guide (e.g., in the form of a table) may be prepared. A kit may be in any suitable form (e.g., a bag of the mixture with a guide/table on the bag).

In yet another exemplary method, the dry cement may be modified based on the value for each of the characteristics measured and analyzed by the optical analysis device (e.g., a concentration of at least one analyte, a relative ratio of two or more analytes, the presence or absences of an analyte, or particle size distribution of the particles in the dry cement). In some instances, modifying may involve blending the dry cement with a second dry cement (e.g., to alter the relative concentration of major components in the dry cement). In some instances, modifying may involve changing the particle size distribution of the dry cement. In some instances, modifying (e.g., during manufacturing) may involve changing the kiln temperature. One of ordinary skill in the art would recognize other suitable modifications that can be made to the dry cement based on the characteristic of interest to achieve a desired dry cement.

In some instances, hybrids of the foregoing methods may be suitable. For example, some embodiments may involve both modifying the dry cement blend and determining a concentration/composition of a cement slurry to add to the dry cement blend after modification. In another example, some embodiments may involve both modifying the dry cement blend and classifying, grading, or both, a cement slurry after modification. In yet another example, some embodiments may involve classifying, grading, or both, a cement slurry to add to the dry cement blend; modifying the dry cement blend; and re-classifying, re-grading, or both, a cement slurry after modification. In some embodiments, each of the foregoing may involve producing a mixture (e.g., a cement slurry) and implementing the mixture in a primary cementing operation, a secondary cementing operation, or a remedial cementing operation in a wellbore.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM, and flash EPROM.

Embodiments disclosed herein include Embodiment A, Embodiment B, Embodiment C, Embodiment D, and Embodiment E.

Embodiment A: A method that includes optically interacting a dry cement with a chemical filter and a detector that together are configured to detect a characteristic of the dry cement, wherein optically interacting the dry cement with the chemical filter comprises absorbing, by the chemical filter, at least a portion of an electromagnetic radiation having optically interacted with the dry cement; generating an output signal corresponding to the characteristic of the dry cement detected by the chemical filter and the detector; receiving and processing the output signal with a signal processor to yield a value for the characteristic of the dry cement; and determining at least one of a composition and a concentration of a cement slurry additive for use in combination with the dry cement based on the value of the characteristic of the dry cement.

Embodiment A may have one or more of the following additional elements in any combination: Element A1: wherein the characteristic of the dry cement is a concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-$, $H_4SiO_4$, a sulfate salt, a phosphate salt, a carbonate salt, a sodium salt, a potassium salt, free lime, a metal containing compound, hydroxide, and water; Element A2: wherein the characteristic of the dry cement is particle size distribution; Element A3: wherein the dry cement is a Portland cement, a hydraulic cement, or a gypsum cement, and wherein the characteristic of the dry cement is a concentration of one selected from the group consisting of $(CaO)_3.SiO_2$, $(CaO)_2.SiO_2$, $(CaO)_3.Al_2O_3$, and $(CaO)_3.Al_2O_3.Fe_2O_3$; Element A4: wherein the dry cement is a Portland cement, a hydraulic cement, or a gypsum cement, and wherein the characteristic of the dry cement is a concentration of one selected from the group consisting of a cadmium compound, a zinc compound, a nickel compound, a copper compound, a lead compound, a sulfate salt, a phosphate salt, a carbonate salt, a sodium salt, and a potassium salt; Element A5: wherein the dry cement is a Sorel cement, and wherein the characteristic of the dry cement is a concentration of one selected from the group consisting of MgO, MgCl2, ZnO, ZnCl2, and water; Element A6: wherein the dry cement is a calcium phosphate cement, and wherein the characteristic of the dry cement is a concentration of one selected from the group consisting of CaO, phosphate, water, and hydroxide; Element A7: wherein the characteristic of the dry cement is a first characteristic of the dry cement, the method further comprising: optically interacting the dry cement with a second chemical filter and either the detector or a second detector, which are configured to detect a second characteristic of the dry cement that is different than the first characteristic of the dry cement; generating a second output signal corresponding to the second characteristic of the dry cement detected by the second chemical filter and either the detector or the second detector; and receiving and processing the second output signal with the signal processor to yield a value for the second characteristic of the dry cement, wherein determining the at least one of a composition and a concentration of the cement slurry additive for use in combination with the dry cement is based on the values for the first and second characteristics of the dry cement; Element A8: Element A7 wherein the second characteristic of the dry cement is a concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-$, $H_4SiO_4$, a sulfate salt, a phosphate salt, a carbonate salt, a sodium salt, a potassium salt, free lime, a metal containing compound, hydroxide, and water; Element A9: the method further including preparing a mixture comprising the dry cement and the cement slurry additive; Element A10: Element A9 further comprising: implementing the mixture in a primary cementing operation, a secondary cementing operation, or a remedial cementing operation in a wellbore; and Element A11: the method further including optically interacting an electromagnetic radiation with the dry cement to produce an optically interacted electromagnetic radiation that then optically interacts with the chemical filter and the detector; and modulating the electromagnetic radiation according to a thermal thickness of a sensing layer in the chemical filter.

By way of non-limiting example, exemplary combinations applicable to Embodiment A include: Element A1 in combination with Element A2 and optionally Element A7 or Element A8; Element A2 in combination with one of Elements A3-A6 and optionally Element A7 or Element A8; one of Elements A3-A6 in combination with Element A7 and optionally Element A8; Element A2 in combination with Element A7 and optionally Element A8; Element A11 in combination with any of the foregoing; and Element A11 in combination with one of Elements A1-A10. Additionally, depending on the number of characteristics of interest, the foregoing combinations may utilize additional chemical filters and detectors.

Embodiment B: A method that includes optically interacting a dry cement with a chemical filter and a detector that together are configured to detect a concentration of $(CaO)_3.SiO_2$, wherein the dry cement is a Portland cement, a hydraulic cement, or a gypsum cement, wherein optically interacting the dry cement with the chemical filter comprises absorbing, by the chemical filter, at least a portion of an electromagnetic radiation having optically interacted with the dry cement; optically interacting the dry cement with a second chemical filter and the detector that together are configured to detect a concentration of $(CaO)_2.SiO_2$, wherein optically interacting the dry cement with the second chemical filter comprises absorbing, by the second chemical filter, at least a portion of the electromagnetic radiation having optically interacted with the dry cement; optically interacting the dry cement with a third chemical filter and the detector that together are configured to detect a concentration of $(CaO)_3.Al_2O_3$, wherein optically interacting the dry cement with the third chemical filter comprises absorbing, by the third chemical filter, at least a portion of the electromagnetic radiation having optically interacted with the dry cement; optically interacting the dry cement with a fourth chemical filter and the detector that together are configured to detect a concentration of $(CaO)_3.Al_2O_3.Fe_2O_3$; generating a plurality of output signals corresponding to each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$, wherein optically interacting the dry cement with the fourth chemical filter comprises absorbing, by the fourth chemical filter, at least a portion of the electromagnetic radiation having optically interacted with the dry cement; receiving and processing the plurality of output signals with at least one signal processor to yield a value for each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; and classifying the dry cement based on the values of each of the concentration of $(CaO)_3.SiO_2$, the concentration of $(CaO)_2.SiO_2$, the concentration of $(CaO)_3.Al2O_3$, and the concentration of $(CaO)_3.Al2O_3.Fe_2O_3$.

Embodiment B may have one or more of the following additional elements in any combination: Element B1: the method further including optically interacting the dry cement with a fifth chemical filter and the detector that together are configured to detect a concentration of one selected from the group consisting of a cadmium compound, a zinc compound, a nickel compound, a copper compound, a lead compound, a sulfate salt, a phosphate salt, a carbonate salt, a sodium salt, and a potassium salt; generating a plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt; receiving and processing the plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt with the at least one signal processor to yield a value for the concentration of one selected from the group consisting of the cadmium compound, the zinc compound, the nickel compound, the copper compound, the lead compound, the sulfate salt, the phosphate salt, the carbonate salt, the sodium salt, and the potassium salt; and grading classifying the dry cement based on the value for the concentration of one selected from the group consisting of the cadmium compound, the zinc compound, the nickel compound, the copper compound, the lead compound, the sulfate salt, the phosphate salt, the carbonate salt, the sodium salt, and the potassium salt; Element B2: the method further including determining at least one of a composition and a concentration of a cement slurry additive for use in combination with the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$; Element B3: the method of Element B2 further including preparing a mixture comprising the dry cement and the cement slurry additive; and Element B4: the method further including modifying the dry cement based on the values of each of the concentration of $(CaO)_3.SiO_2$, the concentration of $(CaO)_2.SiO_2$, the concentration of $(CaO)_3.Al_2O_3$, and the concentration of $(CaO)_3.Al_2O_3.Fe_2O_3$.

By way of non-limiting example, exemplary combinations applicable to Embodiment B include: Element B1 in combination with Element B4 and optionally Elements B2 or B3; Element B1 in combination with Element B2 and optionally Element B3; and Element B4 in combination with Element B2 and optionally Element B3. Additionally, depending on the number of characteristics of interest, the foregoing combinations may utilize additional chemical filters and detectors.

Embodiment C: A method that includes optically interacting a dry cement with a chemical filter and a detector that together are configured to detect a characteristic of the dry cement, wherein the dry cement comprises a minor component selected from the group consisting of $SiO_2$, $Al_2O_3$, $FeO$, $Fe_2O_3$, $CaO$, $Na_2O$, $K_2O$, $MgO$, $SO_3$, $Mn_2O_3$, $TiO_2$, $P_2O_5$, $SnO$, $SrO$, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4$, $H_4SiO_4$, a sulfate salt, a phosphate salt, a carbonate salt, a sodium salt, a potassium salt, free lime, a metal containing compound, hydroxide, water, and any combination thereof, and wherein the characteristic of the dry cement is a concentration of the minor component; generating an output signal corresponding to the characteristic of the dry cement detected by the chemical filter and the detector; receiving and processing the output signal with a signal processor to yield a value for the characteristic of the dry cement; and grading the dry cement based on the value of the characteristic of the dry cement.

Embodiment C may have one or more of the following additional elements in any combination: Element C1: the method further including determining at least one of a composition and a concentration of a cement slurry additive for use in combination with the dry cement based on the value of the characteristic of the dry cement; Element C2: the method of Element C1 further including preparing a mixture comprising the dry cement and the cement slurry additive; and Element C3: the method further including modifying the dry cement based on the value of the characteristic of the dry cement.

By way of non-limiting example, exemplary combinations applicable to Embodiment C include: Element C1 in combination with Element C2 and optionally Element C3; Element C1 in combination with Element C3; and Element C2 in combination with Element C3. Additionally, depending on the number of characteristics of interest, the foregoing combinations may utilize additional chemical filters and detectors.

Embodiment D: A system that includes an optical analysis device having at least one chemical filter and at least one detector together configured (1) to receive electromagnetic radiation having optically interacted with a dry cement that corresponds to a characteristic of the dry cement and (2) to generate an output signal corresponding to the characteristic of the dry cement, wherein the at least one chemical filter is configured to absorb at least a portion of the received electromagnetic radiation having optically interacted with the dry cement.

Embodiment D may have one or more of the following additional elements in any combination: Element D1: wherein the chemical filter comprises a sensing layer having a plurality of layers of material, each layer of material having an optical thickness in a portion of the spectrum according to a regression vector associated with the characteristic of the dry cement; Element D2: wherein the detector is a thermal detector and the chemical filter comprises a sensing layer that is optically sensitive to the optically interacted electromagnetic radiation, the sensing layer optically decoupled from the thermal detector via a reflecting layer; and Element D3: Element D2 wherein the reflecting layer is configured to thermally couple the sensing layer with the thermal detector.

By way of non-limiting example, exemplary combinations applicable to Embodiment D include: Element D1 in combination with Element D2 and optionally Element D3; Element D1 in combination with Element D3; and Element D2 in combination with Element D3. Additionally, depending on the number of characteristics of interest, the foregoing combinations may utilize additional chemical filters and detectors within the optical analysis device or additional optical analysis devices.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Therefore, the exemplary embodiments described herein are well adapted to attain the ends and advantages mentioned as well as those that are inherent therein. The particular embodiments disclosed above are illustrative only, as the exemplary embodiments described herein may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The invention claimed is:

1. A method comprising:
optically interacting a dry cement with a chemical filter and a detector that together are configured to detect a characteristic of the dry cement, wherein optically interacting the dry cement with the chemical filter comprises absorbing, by the chemical filter, at least a portion of an electromagnetic radiation having optically interacted with the dry cement;
generating an output signal corresponding to the characteristic of the dry cement detected by the chemical filter and the detector;
receiving and processing the output signal with a signal processor to yield a value for the characteristic of the dry cement; and
determining at least one of a composition and a concentration of a cement slurry additive for use in combination with the dry cement based on the value of the characteristic of the dry cement,
wherein the dry cement is one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3.SiO_2$, $(CaO)_2.SiO_2$, $(CaO)_3.Al_2O_3$, $(CaO)_3.Al_2O_3.Fe_2O_3$, $CaSO_4.H_2O$, $Ca(OH)_2$, $Al(OH)_4^-$, $H_4SiO_4$, a sulfate salt, a phosphate salt, a carbonate salt, a sodium salt, a potassium salt, free lime, a metal containing compound, hydroxide, and water.

2. The method of claim 1, wherein the characteristic of the dry cement is a concentration of one selected from the dry cement.

3. The method of claim 1, wherein the characteristic of the dry cement is particle size distribution.

4. The method of claim 1, wherein the dry cement is a Portland cement, a hydraulic cement, or a gypsum cement, and wherein the characteristic of the dry cement is a concentration of one selected from the group consisting of $(CaO)_3.SiO_2$, $(CaO)_2.SiO_2$, $(CaO)_3.Al_2O_3$, and $(CaO)_3.Al_2O_3.Fe_2O_3$.

5. The method of claim 1, wherein the dry cement is a Portland cement, a hydraulic cement, or a gypsum cement, and wherein the characteristic of the dry cement is a concentration of one selected from the group consisting of a cadmium compound, a zinc compound, a nickel compound, a copper compound, a lead compound, a sulfate salt, a phosphate salt, a carbonate salt, a sodium salt, and a potassium salt.

6. The method of claim 1, wherein the dry cement is a Sorel cement, and wherein the characteristic of the dry cement is a concentration of one selected from the group consisting of MgO, $MgCl_2$, ZnO, $ZnCl_2$, and water.

7. The method of claim 1, wherein the dry cement is a calcium phosphate cement, and wherein the characteristic of the dry cement is a concentration of one selected from the group consisting of CaO, phosphate, water, and hydroxide.

8. The method of claim 1, wherein the characteristic of the dry cement is a first characteristic of the dry cement, the method further comprising:
optically interacting the dry cement with a second chemical filter and either the detector or a second detector, which are configured to detect a second characteristic of the dry cement that is different than the first characteristic of the dry cement;
generating a second output signal corresponding to the second characteristic of the dry cement detected by the second chemical filter and either the detector or the second detector; and
receiving and processing the second output signal with the signal processor to yield a value for the second characteristic of the dry cement, wherein determining the at least one of a composition and a concentration of the cement slurry additive for use in combination with the dry cement is based on the values for the first and second characteristics of the dry cement.

9. The method of claim 8, wherein the second characteristic of the dry cement is a concentration of one selected from the group consisting of $SiO_2$, $Al_2O_3$, FeO, $Fe_2O_3$, CaO, Na$_2$O, K$_2$O, MgO, SO$_3$, Mn$_2$O$_3$, TiO$_2$, P$_2$O$_5$, SnO, SrO, (CaO)$_3$.SiO$_2$, (CaO)$_2$ SiO$_2$, (CaO)$_3$.Al$_2$O$_3$, (CaO)$_3$.Al$_2$O$_3$.Fe$_2$O$_3$, CaSO$_4$.H$_2$O, Ca(OH)$_2$, Al(OH)$_4$, H$_4$SiO$_4$, a sulfate salt, a phosphate salt, a carbonate salt, a sodium salt, a potassium salt, free lime, a metal containing compound, hydroxide, and water.

10. The method of claim 1, further comprising:
preparing a mixture comprising the dry cement and the cement slurry additive.

11. The method of claim 10, further comprising:
implementing the mixture in a primary cementing operation, a secondary cementing operation, or a remedial cementing operation in a wellbore.

12. The method of claim 1, further comprising modulating the optically interacted light with the dry cement at a modulation frequency selected according to a desired thermal thickness of a sensing layer in the chemical filter.

13. A method comprising:
optically interacting a dry cement with a chemical filter and a detector that together are configured to detect a concentration of (CaO)$_3$.SiO$_2$, wherein the dry cement is a Portland cement, a hydraulic cement, or a gypsum cement, wherein optically interacting the dry cement with the chemical filter comprises absorbing, by the chemical filter, at least a portion of an electromagnetic radiation having optically interacted with the dry cement;
optically interacting the dry cement with a second chemical filter and the detector that together are configured to detect a concentration of (CaO)$_2$.SiO$_2$, wherein optically interacting the dry cement with the second chemical filter comprises absorbing, by the second chemical filter, at least a portion of the electromagnetic radiation having optically interacted with the dry cement;
optically interacting the dry cement with a third chemical filter and the detector that together are configured to detect a concentration of (CaO)$_3$.Al$_2$O$_3$, wherein optically interacting the dry cement with the third chemical filter comprises absorbing, by the third chemical filter, at least a portion of the electromagnetic radiation having optically interacted with the dry cement;
optically interacting the dry cement with a fourth chemical filter and the detector that together are configured to detect a concentration of (CaO)$_3$.Al$_2$O$_3$.Fe$_2$O$_3$, wherein optically interacting the dry cement with the fourth chemical filter comprises absorbing, by the fourth chemical filter, at least a portion of the electromagnetic radiation having optically interacted with the dry cement;
generating a plurality of output signals corresponding to each of the concentration of (CaO)$_3$.SiO$_2$, the concentration of (CaO)$_2$.SiO$_2$, the concentration of (CaO)$_3$.Al$_2$O$_3$, and the concentration of (CaO)$_3$.Al$_2$O$_3$.Fe$_2$O$_3$;
receiving and processing the plurality of output signals with at least one signal processor to yield a value for each of the concentration of (CaO)$_3$.SiO$_2$, the concentration of (CaO)$_2$.SiO$_2$, the concentration of (CaO)$_3$.Al$_2$O$_3$, and the concentration of (CaO)$_3$.Al$_2$O$_3$.Fe$_2$O$_3$; and
classifying the dry cement based on the values of each of the concentration of (CaO)$_3$.SiO$_2$, the concentration of (CaO)$_2$.SiO$_2$, the concentration of (CaO)$_3$.Al$_2$O$_3$, and the concentration of (CaO)$_3$.Al$_2$O$_3$.Fe$_2$O$_3$.

14. The method of claim 13 further comprising:
optically interacting the dry cement with a fifth chemical filter and the detector that together are configured to detect a concentration of one selected from the group consisting of a cadmium compound, a zinc compound, a nickel compound, a copper compound, a lead compound, a sulfate salt, a phosphate salt, a carbonate salt, a sodium salt, and a potassium salt;
generating a plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt;
receiving and processing the plurality of output signals corresponding to the concentration of one selected from the group consisting of the cadmium compound, the zinc compound, the nickel compound, the copper compound, the lead compound, the sulfate salt, the phosphate salt, the carbonate salt, the sodium salt, and the potassium salt with the at least one signal processor to yield a value for the concentration of one selected from the group consisting of the cadmium compound, the zinc compound, the nickel compound, the copper compound, the lead compound, the sulfate salt, the phosphate salt, the carbonate salt, the sodium salt, and the potassium salt; and
grading classifying the dry cement based on the value for the concentration of one selected from the group consisting of the cadmium compound, the zinc compound, the nickel compound, the copper compound, the lead compound, the sulfate salt, the phosphate salt, the carbonate salt, the sodium salt, and the potassium salt.

15. The method of claim 13 further comprising:
determining at least one of a composition and a concentration of a cement slurry additive for use in combination with the dry cement based on the values of each of the concentration of (CaO)$_3$.SiO$_2$, the concentration of (CaO)$_2$.SiO$_2$, the concentration of (CaO)$_3$.Al$_2$O$_3$, and the concentration of (CaO)$_3$.Al$_2$O$_3$.Fe$_2$O$_3$.

16. The method of claim 15 further comprising:
preparing a mixture comprising the dry cement and the cement slurry additive.

17. The method of claim 13 further comprising:
modifying the dry cement based on the values of each of the concentration of (CaO)$_3$.SiO$_2$, the concentration of (CaO)$_2$.SiO$_2$, the concentration of (CaO)$_3$.Al$_2$O$_3$, and the concentration of (CaO)$_3$.Al$_2$O$_3$.Fe$_2$O$_3$.

18. A method comprising:
optically interacting a dry cement with a chemical filter and a detector that together are configured to detect a characteristic of the dry cement, wherein the dry cement comprises a minor component selected from the group consisting of SiO$_2$, Al$_2$O$_3$, FeO, Fe$_2$O$_3$, CaO, Na$_2$O, K$_2$O, MgO, SO$_3$, Mn$_2$O$_3$, TiO$_2$, P2O$_5$, SnO, SrO, (CaO)$_3$.SiO$_2$, (CaO)$_2$.SiO$_2$, (CaO)$_3$.Al$_2$O$_3$, (CaO)$_3$.Al$_2$O$_3$.Fe$_2$O$_3$, CaSO$_4$.H$_2$O, Ca(OH)$_2$, Al(OH)$_4$, H$_4$SiO$_4$, a sulfate salt, a phosphate salt, a carbonate salt, a sodium salt, a potassium salt, free lime, a metal containing compound, hydroxide, water, and any combination thereof, wherein the characteristic of the dry cement is a concentration of the minor component, and wherein optically interacting the dry cement with the chemical filter comprises absorbing, by the chemical filter, at least a portion of an electromagnetic radiation having optically interacted with the dry cement;
generating an output signal corresponding to the characteristic of the dry cement detected by the chemical filter and the detector;

receiving and processing the output signal with a signal processor to yield a value for the characteristic of the dry cement; and grading the dry cement based on the value of the characteristic of the dry cement.

19. The method of claim 18 further comprising:

determining at least one of a composition and a concentration of a cement slurry additive for use in combination with the dry cement based on the value of the characteristic of the dry cement.

20. A system, comprising:

an optical analysis device having at least one chemical filter and at least one detector together configured (1) to receive electromagnetic radiation having optically interacted with a dry cement that corresponds to a characteristic of the dry cement, and (2) to generate an output signal corresponding to the characteristic of the dry cement, wherein the at least one chemical filter is configured to absorb at least a portion of the received electromagnetic radiation having optically interacted with the dry cement, wherein the characteristic of the dry cement is a concentration of one selected from the group consisting of $SiO_2$, $Al_2O_3$, FeO, $Fe_2O_3$, CaO, $Na_2O$, $K_2O$, MgO, $SO_3$, $Mn_2O_3$, $TiO_2$, $P_2O_5$, SnO, SrO, $(CaO)_3 \cdot SiO_2$, $(CaO)_2 \, SiO_2$, $(CaO)_3 \cdot Al_2O_3$, $(CaO)_3 \cdot Al_2O_3 \cdot Fe_2O_3$, $CaSO_4 \cdot H_2O$, $Ca(OH)_2$, $Al(OH)_4^-$, $H_4SiO_4$, a sulfate salt, a phosphate salt, a carbonate salt, a sodium salt, a potassium salt, free lime, a metal containing compound, hydroxide, and water.

* * * * *